(12) United States Patent
Mazzell, Jr. et al.

(10) Patent No.: US 8,729,316 B2
(45) Date of Patent: May 20, 2014

(54) PROCESS FOR PREPARING FLUORINATED DIOLS

(75) Inventors: Paul Mazzell, Jr., Aiken, SC (US); Neville Pavri, Evans, GA (US); Joel Swinson, Evans, GA (US)

(73) Assignee: Halocarbon Products Corporation, River Edge, NJ (US)

( * ) Notice: Subject to any disclaimer, the term of this patent is extended or adjusted under 35 U.S.C. 154(b) by 0 days.

(21) Appl. No.: 13/985,588

(22) PCT Filed: Feb. 16, 2012

(86) PCT No.: PCT/US2012/025396
§ 371 (c)(1),
(2), (4) Date: Aug. 30, 2013

(87) PCT Pub. No.: WO2012/112751
PCT Pub. Date: Aug. 23, 2012

(65) Prior Publication Data
US 2013/0338404 A1    Dec. 19, 2013

Related U.S. Application Data

(60) Provisional application No. 61/443,297, filed on Feb. 16, 2011.

(51) Int. Cl.
*C07C 29/141*    (2006.01)
*C07C 29/145*    (2006.01)

(52) U.S. Cl.
CPC .................................. *C07C 29/145* (2013.01)
USPC ........................................................ 568/842

(58) Field of Classification Search
CPC .. C07C 29/145; C07C 31/205; C07C 31/207; C07C 31/274; C07C 31/276; C07C 31/38; C07C 31/42; C07C 31/44
USPC ........................................................ 568/842
See application file for complete search history.

(56) References Cited

U.S. PATENT DOCUMENTS

| | | |
|---|---|---|
| 3,365,504 A | 1/1968 | Vitcha et al. |
| 3,394,204 A | 7/1968 | Blaga et al. |
| 3,440,285 A | 4/1969 | Lichstein et al. |
| 3,662,071 A | 5/1972 | Langkammerer et al. |
| 7,067,691 B2 | 6/2006 | Komata et al. |
| 7,442,828 B2 | 10/2008 | Breyta et al. |
| 7,495,135 B2 | 2/2009 | Breyta et al. |
| 2005/0215836 A1 | 9/2005 | Komata et al. |

OTHER PUBLICATIONS

International Search Report for PCT/US2012/025396 dated May 29, 2012.

*Primary Examiner* — Elvis O Price
(74) *Attorney, Agent, or Firm* — Norris McLaughling & Marcus, P.A.

(57) ABSTRACT

A process for preparing a fluorinated diol compound by reacting the corresponding ketone-alcohol or aldehyde-alcohol with hydrogen over a palladium catalyst in the vapor phase.

22 Claims, No Drawings

PROCESS FOR PREPARING FLUORINATED DIOLS

This application is a 371 of International Patent Application No. PCT/US2012/025396, filed Feb. 16, 2012, which claims priority benefit under 35 U.S.C. §119(e) of U.S. Provisional Patent Application Ser. No. 61/443,927, filed Feb. 16, 2011, the disclosures of which are incorporated herein by reference.

BACKGROUND OF THE INVENTION

1. Field of the Invention

The present invention relates to a process for preparing fluorinated diol compounds by hydrogenating fluorinated precursor compounds.

2. Description of Related Art

There has been significant interest recently in the synthesis of fluorine containing diol molecules. These fluorinated diols have been used as precursors in the synthesis of monomers for the next generation of photoresist materials, for example, as described in U.S. Pat. Nos. 7,067,691, 7,495,135, and 7,442,828.

The fluorinated diols can be made by the reaction of hexafluoroacetone with various carbonyl compounds followed by the reduction of the carbonyl group to make the desired fluorinated diols. The fluorinated diols can be converted into their acrylate/methacrylate esters for use as monomers.

U.S. Pat. No. 3,662,071 teaches a process for the synthesis of various fluorinated diols (Scheme I) by (1) reacting hexafluoroacetone (or chlorodifluoro acetone) with a suitable ketone at 160° C. and (2) reducing the keto-alcohol made in step 1 with aluminum isopropoxide and isopropanol. This reduction method has the drawback of generating significant aluminum waste that has to be disposed of. This leads to a lower yield because some of the organic product is left behind in aqueous phase and there is an increased cost associated with getting rid of the aluminum waste.

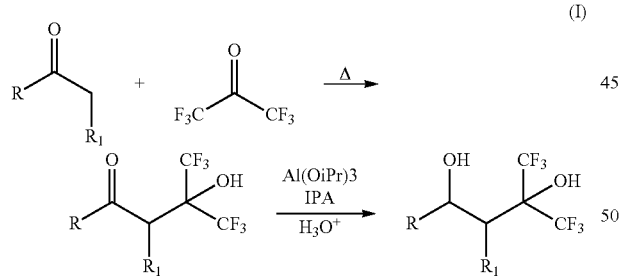

(I)

U.S. Pat. No. 7,205,443 solves this problem (Scheme II) by reducing the keto alcohol made by reaction of hexafluoroacetone and carbonyl compound, with hydrogen, over ruthenium catalyst.

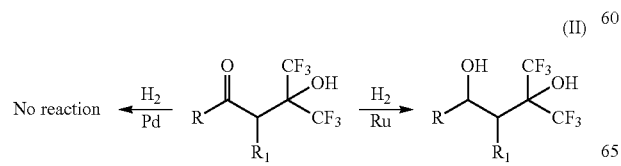

(II)

This patent further teaches that this reduction can only be effected using ruthenium as catalyst. The patentees mention that the use of palladium and platinum gave poor results. An example from the experimental section shows less than 5% conversion with platinum as the catalyst and essentially no conversion using Pd as the hydrogenation catalyst (Scheme II).

U.S. Pat. No. 3,440,285 claims a process of reacting aliphatic aldehydes with fluorinated ketones such as hexafluoroacetone to generate fluorinated hydroxy substituted aldehydes. These hydroxy aldehydes were then reduced to fluorinated diols using known reagents like lithium aluminum hydride, sodium borohydride, lithium borohydride or aluminum isopropoxide (Scheme III). These reduction methods are either not easily scalable or generate significant metal waste by-products. This patent also teaches that the reduction of the hydroxy aldehyde can be achieved by hydrogenation over rhodium, platinum or using Raney nickel catalyst. No mention is made of using the much cheaper palladium as a catalyst to affect this transformation.

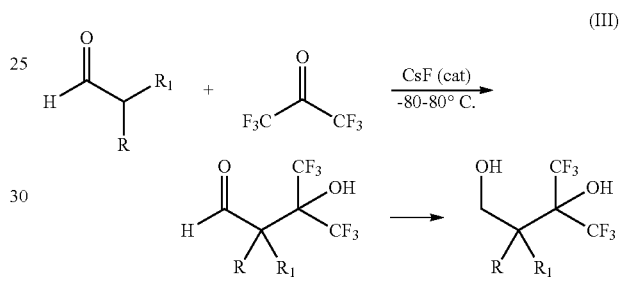

(III)

What is needed is a cleaner process that does not generate waste and that is preferably continuous and uses less expensive catalyst.

SUMMARY OF THE INVENTION

These and other objects were met with the present invention, which relates in a first embodiment to a process for preparing a fluorinated diol compound of the formula:

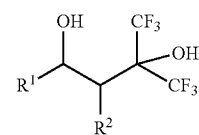

in which
$R^1$ represents hydrogen, optionally substituted alkyl or optionally substituted cycloalkyl; and
$R^2$ represents hydrogen, optionally substituted alkyl or optionally substituted cycloalkyl;
said process comprising reacting a fluorinated precursor compound of the formula:

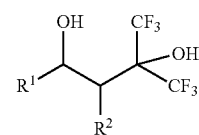

in which $R^1$ and $R^2$ have the meaning given above, with hydrogen over a palladium catalyst in the vapor phase.

Surprisingly, we have discovered that the reaction above in the vapor phase gives a very good conversion and yield in direct contrast to the teachings of the patents described above.

DETAILED DESCRIPTION OF THE INVENTION

The reaction proceeds to very good conversion and yield particularly where in the formula above $R^1$ represents H or $C_{1-8}$-alkyl; and $R^2$ represents H, $C_{1-8}$-alkyl, halogenated $C_{1-8}$-alkyl, $C_{3-6}$-cycloalkyl or halogenated $C_{3-6}$-cycloalkyl. In a very particularly preferred embodiment, $R^1$ represents H; and $R^2$ represents H or $C_{1-4}$-alkyl. In an especially preferred embodiment, $R^1$ represents H; and $R^2$ represents H. Conversions on the order of greater than 90%, preferably greater than 95%, most preferably greater than 99%; and yields of greater than 90%, preferably greater than 95%, can be expected when $R^1$ is hydrogen. Conversions on the order of 5%, possibly more; and yields of greater than 90%, preferably greater than 95%, can be expected when $R^1$ is other than hydrogen.

The palladium catalyst is supported or unsupported. In one embodiment, the palladium catalyst is unsupported. In another embodiment, the palladium catalyst is supported on any suitable support. In a particularly preferred embodiment, the palladium catalyst is supported on a support selected from the group consisting of activated carbon, alumina and silica. In an especially preferred embodiment, the palladium catalyst is supported on an activated carbon support.

The amount of the catalyst on the support can vary within a large range, as already well known in the art. In the especially preferred embodiment, wherein the palladium catalyst is supported on an activated carbon support, a preferred range is that the palladium on activated carbon catalyst is present in a concentration of 0.5 to 20% by weight, based on the total weight of the catalyst.

Catalyst bed temperature can also vary in the manner well known in the art. In a preferred embodiment, the catalyst is contained in a catalyst bed at a temperature between 100-350° C. In an especially preferred embodiment, the temperature of the catalyst bed is between 150-250° C.

In a preferred embodiment, the inventive process is run at a pressure between 0-150 psi (0-1033.5 kPa gauge). In an especially preferred embodiment, the pressure ranges from 10-50 psi (68.9-344.5 kPa gauge).

The amount of hydrogen reacted is preferably 1-10 mole equivalents, based on the amount of precursor compound. In an especially preferred embodiment, the amount of hydrogen reacted is 1-5 mole equivalents, based on the amount of precursor compound.

It is preferred that the precursor compound is vaporized before the precursor compound is contacted with the palladium catalyst, but this is not absolutely necessary. Whenever the precursor compound is vaporized, the precursor compound is or is not vaporized in admixture with a solvent If the precursor compound is vaporized in admixture with a solvent, the solvent is selected from the group consisting of ethers and alcohols. Preferably, the solvent is selected from the group consisting of tertiary-butyl methyl ether, methanol, ethanol and isopropanol.

The inventive process may be carried out as a batch process or a continuous process. In one preferred embodiment, the inventive process is carried out as a batch process. In an particularly preferred embodiment, the inventive process is carried out as a continuous process.

The precursor compound is well known in the art and may be prepared by any known preparation scheme. In a preferred embodiment, the precursor compound is prepared by a process comprising reacting a compound of the formula:

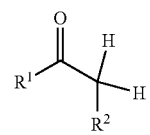

with hexafluoroacetone of the formula:

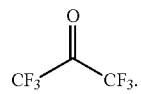

Where $R^1$ is hydrogen, the preparation of the precursor compound can be prepared using the procedure set forth in U.S. Pat. No. 3,440,285, the entire contents of which are incorporated herein by reference.

Where $R^1$ is other than hydrogen, the preparation of the precursor compound can be prepared using the procedure set forth in U.S. Pat. No. 3,662,071, the entire contents of which are incorporated herein by reference.

The invention will now be described in greater detail with reference to the following:

EXAMPLE

A 6 feet long tube that was 1 inch in diameter was packed with 2% Pd on carbon. The tube was heated to 170° C. and a mixture of 1, 1, 1-Trifluoro-2-trifluoromethyl-2-hydroxy-4-butanal (hydroxy aldehyde) and 10% by weight of t-butyl methyl ether was co-vaporized and fed down the hot-tube with 5 mole equivalents of hydrogen gas. The gaseous mixture was fed down the hot-tube under 10 psi (68.9 kPa gauge) pressure and at a rate of 1.0 moles/hr. of the hydroxy aldehyde. The yield of the desired 1, 1, 1-Trifluoro-2-trifluoromethyl-2, 4-butanediol (butanediol) was 99%.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A process for preparing a fluorinated diol compound of the formula:

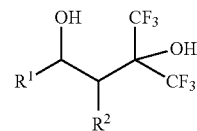

in which
$R^1$ represents hydrogen, optionally substituted alkyl or optionally substituted cycloalkyl; and
$R^2$ represents hydrogen, optionally substituted alkyl or optionally substituted cycloalkyl;
said process comprising reacting a fluorinated precursor compound of the formula:

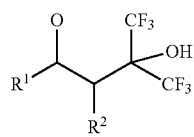

in which $R^1$ and $R^2$ have the meaning given above, with hydrogen over a palladium catalyst in the vapor phase.

2. The process according to claim 1, wherein $R^1$ represents H or $C_{1-8}$-alkyl; and $R^2$ represents H, $C_{1-8}$-alkyl, halogenated $C_{1-8}$-alkyl, $C_{3-6}$-cycloalkyl or halogenated $C_{3-6}$-cycloalkyl.

3. The process according to claim 1, wherein $R^1$ represents H; and $R^2$ represents H or $C_{1-4}$-alkyl.

4. The process according to claim 1, wherein $R^1$ represents H; and $R^2$ represents H.

5. The process according to claim 1, wherein the palladium catalyst is supported or unsupported.

6. The process according to claim 5, wherein the palladium catalyst is supported on a support selected from the group consisting of activated carbon, alumina and silica.

7. The process according to claim 6, wherein the palladium catalyst is supported on an activated carbon support.

8. The process according to claim 7, wherein the palladium on activated carbon catalyst is present in a concentration of 0.5 to 20% by weight, based on the total weight of the catalyst.

9. The process according to claim 1, wherein the catalyst is contained in a catalyst bed at a temperature between 100-350° C.

10. The process according to claim 9, wherein the temperature of the catalyst bed is between 150-250° C.

11. The process according to claim 1, which is run at a pressure between 0-1033.5 kPa gauge.

12. The process according to claim 11, which is run at a pressure between 68.9-344.5 kPa gauge.

13. The process according to claim 1, wherein the amount of hydrogen reacted is 1-10 mole equivalents, based on the amount of precursor compound.

14. The process according to claim 13, wherein the amount of hydrogen reacted is 1-5 mole equivalents, based on the amount of precursor compound.

15. The process according to claim 1, wherein the precursor compound is vaporized before the precursor compound is contacted with the palladium catalyst.

16. The process according to claim 1, wherein the precursor compound is or is not vaporized in admixture with a solvent.

17. The process according to claim 16, wherein the precursor compound is vaporized in admixture with a solvent.

18. The process according to claim 17, wherein the solvent is selected from the group consisting of ethers and alcohols.

19. The process according to claim 18, wherein the solvent is selected from the group consisting of tertiary-butyl methyl ether, methanol, ethanol and isopropanol.

20. The process according to claim 1, which is carried out as a batch process or a continuous process.

21. The process according to claim 20, which is carried out as a continuous process.

22. The process according to claim 1, wherein the precursor compound is prepared by a process comprising reacting a compound of the formula:

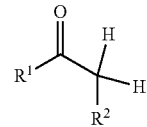

with hexafluoroacetone of the formula:

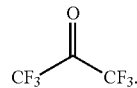

* * * * *